United States Patent [19]
McClure et al.

[11] Patent Number: 6,027,217
[45] Date of Patent: Feb. 22, 2000

[54] AUTOMATED VISUAL FUNCTION TESTING VIA TELEMEDICINE

[75] Inventors: Richard J. McClure; Dariusz Wroblewski, both of San Diego; R. Kemp Massengill, Leucadia, all of Calif.

[73] Assignees: Virtual-Eye.com, Inc., Leucadia; Orincon Corp., San Diego, both of Calif.

[21] Appl. No.: 09/179,112

[22] Filed: Oct. 26, 1998

Related U.S. Application Data

[63] Continuation-in-part of application No. 08/700,754, Jul. 31, 1996, Pat. No. 5,864,384, which is a continuation-in-part of application No. 08/864,331, May 28, 1997, Pat. No. 5,898,474.

[60] Provisional application No. 60/067,521, Dec. 4, 1997, and provisional application No. 60/089,817, Jun. 19, 1998.

[51] Int. Cl.$^7$ ......................................................... A61B 3/02
[52] U.S. Cl. ............................................. 351/224; 351/246
[58] Field of Search ..................................... 351/224, 226, 351/222, 237, 239, 246

[56] References Cited

U.S. PATENT DOCUMENTS

| | | | |
|---|---|---|---|
| 5,061,059 | 10/1991 | Horn ........................................ | 351/223 |
| 5,325,136 | 6/1994 | Salibello et al. ......................... | 351/243 |
| 5,565,949 | 10/1996 | Kasha, Jr. ................................ | 351/224 |
| 5,758,651 | 6/1998 | Nygard et al. ........................... | 128/741 |
| 5,864,384 | 1/1999 | McClure et al. ......................... | 351/224 |
| 5,867,494 | 2/1999 | Krishnaswamy et al. ............... | 370/352 |

FOREIGN PATENT DOCUMENTS

| | | |
|---|---|---|
| 0 850 661 | 7/1998 | European Pat. Off. . |
| 0 856 333 | 8/1998 | European Pat. Off. . |
| 0 857 455 | 8/1998 | European Pat. Off. . |

OTHER PUBLICATIONS

Alboliras, E.; Transmission of Full–Length Echocardiographic Images over ISDN for Diagnosing Congenital Heart Disease; 1996; Telemedicine Journal vol. 2, No. 4; pp251–258. .

Angood, P.; Internet–based Telemedicine: A Practical Tool ?; 1998; Medicine Meets Virtual Reality; pp. 383–384.

Bashshur, R.; *Telemedicine;* date unknown; pp. 309–347.

Bekker, M.; *Exploring Telemedicine;* date unknown; 6 pages.

Bethke, W.; The Internet vs. Glaucoma; Nov. 1997; Review of Ophthalmology; p. 19.

Blackwell, N.; Telemedicine Ophthalmology Consultation in Remote Queensland; Apr. 1997; Medicinal Journal of Australia, 6 pages.

Defense Department Awards Telemedicine Ophthalmolmic Technology Contract, May 1997; Telemedicine and Virtual Reality; p. 53.

Dicon brochure; *The Future: Visual Fields Across the Information Superhighway;* Aug. 1998; 1 page.

Grigsby, J.; Effects and Effectiveness of Telemedicine; 1995; Health Care Financing Review; pp. 1–18.

Grigsby, J.; Telemedicine: Where It Is and Where It's Going; Jul. 1998; Annals of Internal Medicine; pp. 123–127.

Heneghan, C.; Teleophthalmology at the New York Eye and Ear Infirmary; Dec. 1996; Telemedicine Today; 3 pages.

(List continued on next page.)

*Primary Examiner*—Huy Mai
*Attorney, Agent, or Firm*—Gerald W. Spinks

[57] ABSTRACT

A method and an apparatus for utilizing a central neural network and a central data bank to perform automatic interpretation of the visual function test parameters obtained in a plurality of visual field testing systems, for a plurality of patients, with control and response signals being transmitted via the Internet. The data produced by the testing systems are automatically analyzed and compared with patterns on which the neural network was previously trained, and clinical diagnoses for pathological conditions are thereby suggested to the respective clinician for each patient.

13 Claims, 3 Drawing Sheets

OTHER PUBLICATIONS

Heneghan, C.; Ophthalmology Rides Wave of Telemedicine; May 1997; Ophthalmology Times; 2 pages.

Heneghan, C.; Clinical Interaction the Key to Telemedicine; Jun. 1997; Ophthalmology Times; 5 pages.

Lindberg, D.; *Medicine and Health on the Internet;* Oct. 21, 1998; Journal of the American Medical Association, vol. 280, No. 15; pp. 1303–1304.

Marcus, D.: Telemedicine Diagnosis of Eye Disorders by Direct Ophthalmoscopy; May 1998; Ophthalmology; pp. 1907–1914.

Mitka, M.; Developing Countries Find Telemedicine Forges Links to More Care and Research; Oct. 21, 1998; Journal of the American Medical Association, vol. 280, No. 15; pp. 1295–1296.

Mutlukan, E.; Visual Field Interpretation with a Personal Computer Based Neural Network; 1994; Eye, vol. 8; pp. 321–323.

Nitzkin, J.; Reliability of Telemedicine Examination; 1997; Telemedicine Journal; pp. 141–157.

Pedersen, S.; Teleconsultation of Patients with Otorhinolaryngologic Conditions; Feb. 1994; Archives of Otolaryngologic Head Neck Surgery, vol. 120; pp. 133, 135, 136.

Sanders, J.; Challenges to the Implementation of Telemedicine; 1995; Telemedicine Journal; pp. 115–123.

Sarasohn–Kahn, J.; Tele–Health; 1996; Medical and Healthcare Marketplace Guide; pp. 43–44.

Schiffman, J.; Practice Makes Perfect: Devising Technical Specs for Tele–ophthalomology; Jun. 1997; Telemedicine, 5 pages.

Singer, H.; *New Perimetry Algorithm Uses Artificial Intelligence to Shorten Test Time;* Nov. 1996; publication unknown; 2 pages.

Telemedicine Targets Mammographic Services; Dec. 1997; Biophotonics International; 1 page.

Teleophthalomology Clinic Gets a Workout; Nov. 1997; Telemedicine and Virtual Reality; p. 132.

Arnold, D. B. The Oculomotor Integrator: Testing of a Neural Network Model; Dec. 1995; Exp Brain Res (1997) 113; pp. 57–74.

Brigatti, Luca; Automatic Detection of Glaucomatous Visual Field Progression with Neural Networks; Jun. 1997; Arch Ophthalmol, vol. 115; pp. 725–728.

Brigatti, L.; Neural Networks to Identify Glaucoma with Structural and Functional Measurements; Nov. 1995; American Journal of Ophthalmology (1996) 121; pp. 511–521.

Gardner, G.; Automatic Detection of Diabetic Retinopathy Using an Artificial Neural Network; A Screening Tool; Jun. 1996; British Journal of Ophthalmology (1996) 80; pp. 940–944.

Goldbaum, Michael H.; Interpretation of Automated Perimetry for Glaucoma by Neural Network; Mar. 1994; Investigative Ophthalmology & Visual Science, Aug. 1994, vol. 35, No. 9; pp. 3362–3373.

Levin, Leonard A.; Neural Network Differentation of Optic Neuritis and Anterior Ischaemic Optic Neuropathy; May 1996; British Journal of Ophthalmology (1996)80; pp. 835–839.

Spenceley, S. E.; Visual Field Analysis Using Artificial Neural Networks; Feb. 1994; Ophthal. Physiol. Opt. 1994, vol. 14; pp. 239–248.

Uchida, Hideya; Detection of Structural Damage from Glaucoma with Confocal Laser Image Analysis; Jul. 1996; Investigative Ophthalmology & Visual Science, Nov. 1996; vol. 37, No. 12; pp. 2393–2401.

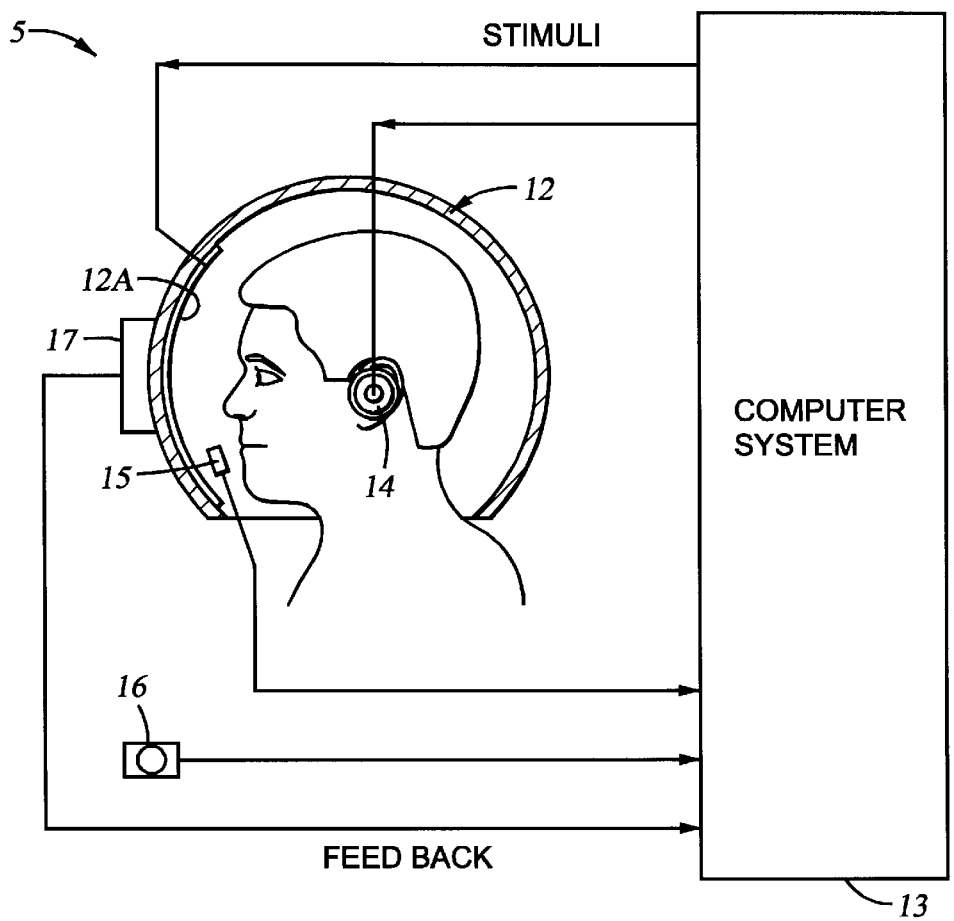
Fig. 1
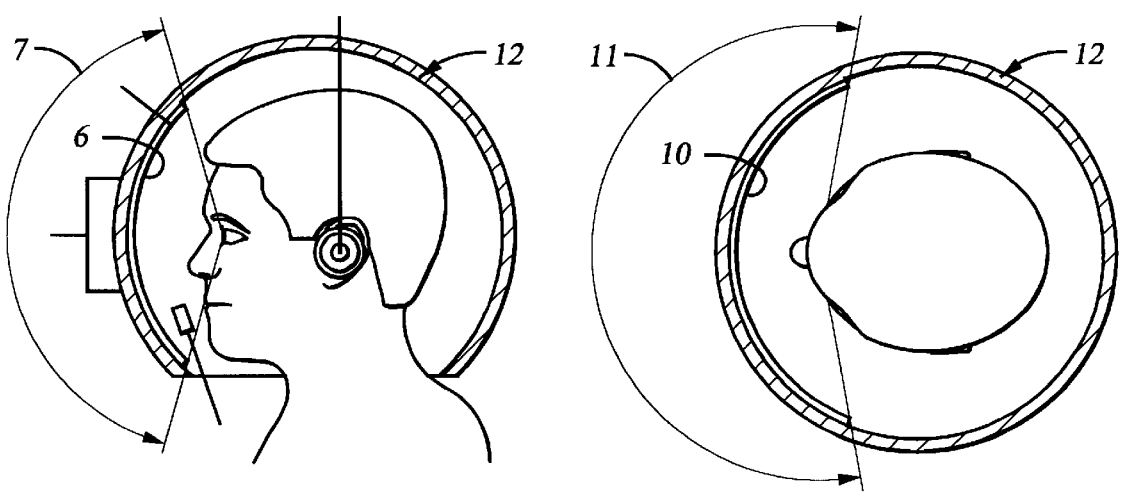
Fig. 2
Fig. 3

AUTOMATED VISUAL FUNCTION TESTING VIA TELEMEDICINE

CROSS REFERENCE TO RELATED APPLICATIONS

This application is a continuation-in-part of prior application Ser. No. 08/700,754, filed Jul. 31, 1996, for Visual Field Testing Method and Apparatus Using Virtual Reality, now U.S. Pat. No. 5,864,384, and prior application Ser. No. 08/864,331, filed May 28, 1997, for Visual Field Testing Method and Apparatus, now U.S. Pat. No. 5,898,474. This application also claims priority from Provisional U.S. patent application Ser. No. 60/067,521, filed Dec. 4, 1997, for Automated Visual Function Testing in Virtual Reality, and Provisional U.S. patent application Ser. No. 60/089,817, filed Jun. 19, 1998, for Telemedicine for Autointerpretation of Visual Field Testing.

STATEMENT REGARDING FEDERALLY SPONSORED RESEARCH OR DEVELOPMENT

Not Applicable

BACKGROUND OF THE INVENTION

1. Field of the Invention

This invention is in the field of performance of visual field tests and other tests of visual function, for the diagnosis of eye conditions.

2. Background Information

On a world-wide basis, glaucoma is one of the leading causes of blindness. Unlike cataract blindness, which is correctable with modern surgical techniques, blindness from glaucoma is permanent. The target organ of glaucoma is the optic nerve, which transmit signals of light from the retina to the brain. No known method is available for repairing, or transplanting, an injured optic nerve.

A major diagnostic problem is that visual loss from glaucoma is almost without exception painless. The patient is not aware of the ravages of glaucoma until it is too late. To compound the problem, the intraocular pressure in glaucoma is often not elevated (termed "low-tension" glaucoma), and therefore reliance upon tonometry to measure the patient's intraocular pressure frequently leads to a blatantly false sense of security. The patient is told that glaucoma is not present, when, in reality, the disease is insidiously attacking the patient's optic nerve, causing irreversible neurological damage to the visual system.

Visual field testing is mandatory for glaucoma diagnosis and treatment. The current gold standard of measurement of optic nerve function is visual field testing, called "perimetry." A problem with this technology, however, is that far too many of the examiners performing visual field testing are inadequately trained to recognize subtle patterns in the patient's visual field indicative of glaucoma (or other neurological disease). Such misdiagnosis, which is unfortunately frequent, again gives the patient a false sense of security.

Millions upon millions of patients throughout the world have glaucoma and are completely unaware of this. The particularly sad aspect of glaucoma blindness is that it is generally preventable with proper diagnosis and treatment. The proposed invention, which incorporates the use of telemedicine for real-time feedback and for autointerpretation of visual field performance, will play a major role in eliminating the all-too-common errors in visual field interpretation and the unnecessary blindness which accompanies such ignorance. By making the proper diagnosis virtually instantaneously over the Internet or other telemetric vehicle, glaucoma treatment can be instituted. Millions of patients will be spared the ravages of glaucoma.

In addition to testing for glaucomatous damage to the optic nerve, visual field testing is also used to test for a variety of neurological disorders, including cerebrovascular accidents ("strokes"), trauma, brain tumors, and other diseases. The proposed invention, which incorporates real-time feedback to monitor the patient's performance, and accurate, instantaneous diagnosis available through autointerpretation on a world-wide telemetric basis, addresses a major medical need.

With the huge data base developed by a large-scale, world-wide telemedicine system, leading international experts on glaucoma and other neurological diseases can be employed to improve the accuracy of the entire system.

Investigational work has been done on the use of neural nets "trained to interpret the visual fields from an automated perimeter," as described in "Interpretation of Automated Perimetry for Glaucoma by Neural Net," by Goldbaum, et al. Spenceley, et al. have also published work in the field in an article entitled, "Visual Field Analysis Using Artificial Neural Networks." Brigatti, Hoffman, and Caprioli have worked with neural networks for glaucoma identification, as described in their article entitled, "Neural Networks to Identify Glaucoma With Structural and Functional Measurements." These works are limited to conventional globe-like perimeter systems.

BRIEF SUMMARY OF THE INVENTION

The presently-described invention uses a data processing system to provide automatic interpretation of visual field and other test data received from testing apparatus in a system which can feature a virtual reality head-mounted display system. Using virtual reality and associated head-gear configuration in an interactive computerized system allows unprecedented freedom of movement of the head and body, thus minimizing or even eliminating the stress and fatigue common with conventional non-virtual reality visual field testing systems.

The combination of automatic visual field interpretation with a head-mounted display system is unique and novel. The use of telemedicine for centralized interpretation of visual field testing at remote locations, and interactively modulating the performance of the patient is likewise unique and novel.

The present invention also contemplates the use of a standard visual field testing machine, utilizing telemedicine between a central station and several remote test sites, for supplying, testing, measuring, quantifying, and autointerpreting visual information to and from the visual pathways of the eye and the retina, the optic nerve, the optic chiasm, the visual pathways to the brain, and the brain itself. A machine such as, for example, those manufactured by Humphrey Instruments, Dicon, or Octopus, can be used to present visual stimuli to a patient. Audio feedback stimuli, such as voice, or a tone or series of tones, or tactile feedback stimuli, such as a vibration, monitor the test performance in real-time. These stimuli are generated and controlled by software in an associated computer, which receives interactive feedback stimuli from the patient. The content of the software is dictated by the need to provide technically acceptable protocols, such as for examining wide and narrow fields of view, selected areas, such as the blind spot or the fovea, and measurements of thresholds for sensitivity to light intensity, or, if desired, color. Active feedback sensing alerts the system to patient loss of attention in general, or loss of fixation in particular, for notation and reiteration of test stimuli. The system is configured to allow test stimuli to be presented to one eye at a time, or to both eyes simultaneously. Individual test points are reiterated when a result is found to be inconsistent with a predetermined norm.

The novel features of this invention, as well as the invention itself, will be best understood from the attached drawings, taken along with the following description, in which similar reference characters refer to similar parts, and in which:

BRIEF DESCRIPTION OF THE SEVERAL VIEWS OF THE DRAWINGS

FIG. 1 is a schematic view of the local test site apparatus used in the present invention;

FIG. 2 is a side view of the apparatus of FIG. 1 measuring a vertical angular field of view;

FIG. 3 is a top view of the apparatus of FIG. 1 measuring a horizontal angular field of view;

DETAILED DESCRIPTION OF THE INVENTION

Figure 4:
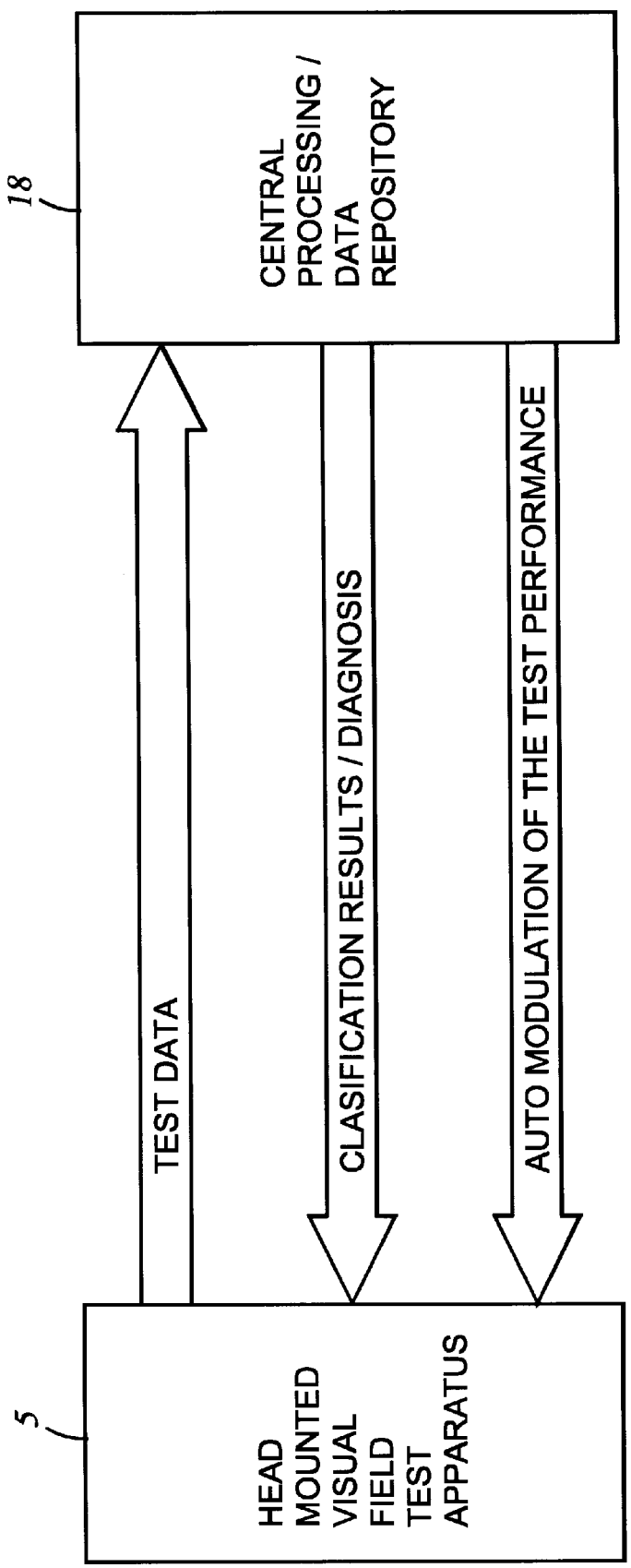
FIG. 4 is a schematic diagram of the information flow in the system of the present invention.

FIG. 1 shows a schematic of one embodiment of the local virtual reality visual field testing apparatus 5 which can be incorporated in the present invention, in which a head-gear assembly 12 is connected to a local or even imbedded processing system 13, which delivers a visual signal to a head-gear display screen 12(a), and an audio signal to a head-gear earphone 14.

The head-mounted visual display apparatus, head-gear 12, which remains in a fixed spatial relationship to the patient's head during testing of the visual field, is adjustable to suit the individual patient, and is mounted on the patients head by conventional means. The screen display 12(a) is part of the head-gear 12 and encompasses the maximum field of view required. The head-gear 12 is provided with an integral microphone 15 and a speaker or earphone 14, for audio communication and feedback, and a multi-element gaze-aim sensor array 17. The microphone 15 provides feedback audio response to the processing system 13. The head-gear assembly 12 is connected, by appropriate means, to the processing system 13 which provides the necessary visual and audio stimuli for the patient, and which receives the feedback responses to enable interactive functioning of the system. A hand-operated switch 16 is incorporated to provide the patient's response feedback to the processing system 13, and the gaze sensor 17, mounted in the direction of gaze, provides optical gaze direction feedback to the processing system 13.

FIG. 2 shows, by dashed line 6, a vertical image surface covering an angular field of view 7 on the screen display 12(a).

FIG. 3 shows, by dashed line 10, a horizontal image surface covering an angular field of view 11 on the screen display 12(a).

An element of the virtual reality visual field testing apparatus 5 is that it allows the patient the freedom to shift his/her gaze, while in the test mode, without disruption of the process, thus relieving one of the causes of patient stress.

Another feature provided is the ability to modulate the background scene brightness, contrast, color, optical stimulus size and detail, and duration of the test stimuli, all of which serve to relieve fatigue of the patient. Of paramount significance is that the patient may move around bodily, since the head gear 12 is portable and, in addition, electrical interfaces to the processing system 13 may be wireless.

In addition to a vastly more patient-friendly and portable test setting, a further significant advantage of the presently-described method and apparatus is that background light intensity and other parameters can be easily calibrated to predetermined settings, thus eliminating the requirement mandated by conventional visual field testers to calibrate these parameters for the entire room. For instance, the fact that room brightness can vary almost imperceptibly, but yet significantly, from day to day in conventional visual field testing situations creates built-in unreliability of the test data received from the patient.

Furthermore, feelings of anxiety frequently displayed by patients undergoing conventional visual field testing in which first one eye and then the fellow eye is covered with an occluder patch can be eliminated in the preferred embodiment, since both eyes can be tested simultaneously, or separately and independently, through the use of individual eye goggles, or an appropriate face mask, to provide gaze separation.

In other embodiments of the present invention, a standard visual field testing machine can be used in lieu of the head-mounted display, where preferred. A local processing system 13 would still be employed, however.

The system of the present invention, as illustrated in FIG. 4, includes a local visual field test apparatus 5, which can include a head mounted visual field test apparatus 12 or a standard visual field testing machine, and a local processing system 13 which can form an integral part of the head-mounted diagnostic apparatus 12. The expert supervision of the testing process and interpretation of the results can be performed via long-distance transmission vehicles, such as, but not limited to, optical fiber or Internet, thus providing, telemetrically, not only essentially instantaneous autointerpretation, but also telemetric monitoring of the patient's performance of the test in real time. A central world-wide processing/data collection system 18 (consisting of a single station or a series of stations, such as one for the United States, one for Japan, one for France, etc.) can be linked via the Internet to a multitude of local test stations 5 and provide multiweb-like integration. Alternatively, as international long-distance communication becomes more and more affordable, one central station could have global capability via direct connection over telephone lines. The data processing portion of the system incorporates the local processing system 13 and the central processing system and data repository 18, to provide the classification of the visual field test data in terms of presence or absence of all diseases, or any particular disease (e.g., glaucoma). The data processing portion of the system also may assign a probability of detection and/or a numerical value indicating the severity of the disease. This provides a tool for monitoring disease progression.

Functions of the local processing system include the following:
(a) provision of visual stimuli,
(b) automatic customization of the stimuli sequence based on the patient response, including repetition of the stimuli for which no adequate response was registered (due either to the patient's loss of attention or to disease-induced damage to the visual field), and adjustment of the amplitude of stimuli, and (c) pre-processing of the patient response data, such as elimination of those measurement points (patient's responses) that are deemed inadequate, normalization to a predefined standard, and formatting for transmission to the remote processing system.

Functions of the remote processing system include the following:

(a) automatic interpretation of the visual field test data, and (b) formulation of corrections to the data collection protocol, based on the results of auto-interpretation and comparative analysis employing the database of interpreted and medically verified visual field tests.

Figure 5:
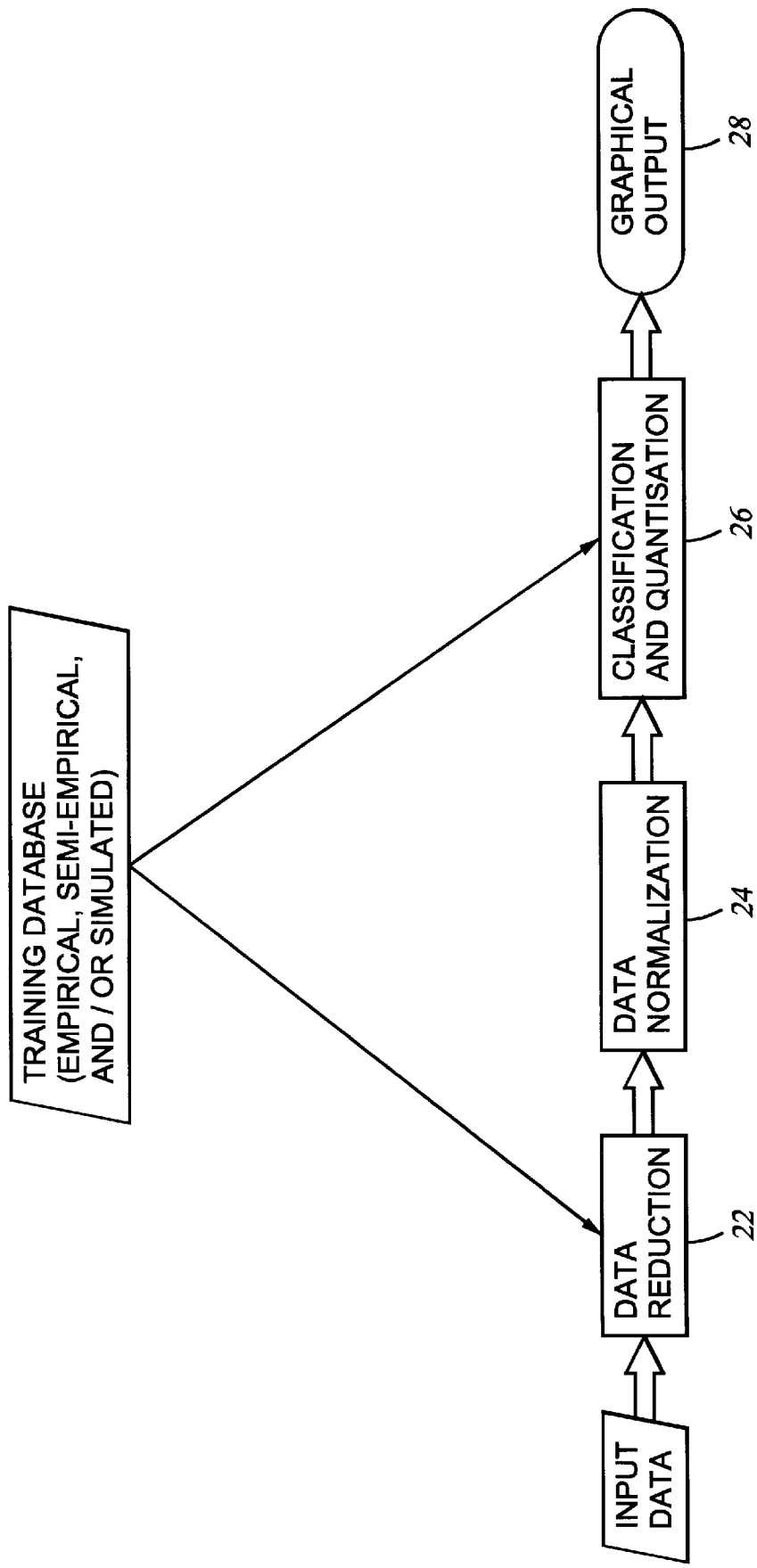
FIG. 5 is a schematic diagram of the automatic interpretation portion of the system of the present invention.

The central processing/data collection system 18 includes an automated interpretation system, incorporating a neural network, which functions as shown in FIG. 5. Integration of a multitude of local testing stations 5 into a world-wide system results in a telemedicine system which is "intelligent" in that ongoing data accumulation and analyses thereof improve the computational model and provide, over time, increasingly more accurate identification of very subtle disease processes.

A database of empirical, semi-empirical, or simulated visual field test data is used to build a neural network model of the visual field test data. This model, when applied to previously unseen test results, is capable of automatically interpreting and classifying the test data in terms of the presence and/or severity of abnormal (diseased) regions and states.

The auto-interpretation system utilizes the results of visual stimuli (consisting of dots, symbols, shapes, or patterns, with or without color, etc.) presented to the patient, which are converted into numerical representation for data processing, such as in the standard automated perimetry schemes (cf. Humphrey Field Analyzer). Other inputs, resulting from standard pre-processing of the test data, such as visual field indices, can also be employed by the neural network. Inclusion of all available individual components of perimetric examination is useful for proper clinical interpretation of the visual test examination. Thus, the information provided to the neural network may include:

(a) ancillary data, such as pupil size during testing, the patient's age, and visual acuity;

(b) reliability indices, such as fixation behavior and accuracy, and response fluctuation;

(c) visual field indices, such as average deviation of sensitivity at each test location from age-adjusted normal population values, the index of the degree of irregularity of visual field sensitivity about the normal slope, and sensitivity analysis of clusters of points;

(d) results of point-by-point comparison of test results with age-matched normal population values;

(e) results of high-pass resolution perimetry, if available from the given implementation of the test apparatus; and, (f) results of pattern discrimination perimetry and other available tests.

The use of the entire gamut of available information for automatic interpretation by the neural network is also novel. Previously known neural network systems included only the straight visual field data.

The preferred embodiment of the neural network based auto-interpretation system is shown in FIG. 5. The system consists of some or all of the modules described below.

The data reduction module 22 is employed to reduce the size of the data vector presented to the neural network classifier. This module employs singular value decomposition, principal component analysis (PCA), learning vector quantization, or other clustering and data size reduction methods. Typically, application of any of these methods results in at least a two-fold decrease in the size of the data vector. Such a reduction increases the ability of the neural network to generalize the data contained in the training set. The clustering and linear decomposition methods (such as PCA) are also useful for 'novelty detection', i.e., for establishing if the current data vector is outside the region encompassed by the training data set. The neural network model is likely to fail for such data and thus, the ability to detect novelty is crucial for minimizing the number of erroneous interpretations.

The data normalization module 24 performs amplitude normalization of the data presented to the neural network.

The neural network classifier module 26 performs pattern recognition and classification of the visual field test data. The probability of classification (or, degree of membership) is quantified for each of the classes considered in the model. In the preferred embodiment, a non-linear classification scheme exemplified by the multilayer perceptron or the radial/ellipsoidal basis function neural network is used. However, other classification schemes such as multivariate analysis, linear regression, statistical classifiers or discriminators (such as Bayesian classifiers) may also be employed. The neural networks are especially useful for the automatic application scheme because they provide a nonparametric, empirical model of the visual field test data and are computationally non-intensive, i.e., the classification computations can be performed quickly on inexpensive computers.

The neural network may be a binary classification system, which will indicate the presence or absence of a particular disease, such as glaucoma, or a multi-class system, which provides recognition and classification of a large variety of possible visual field disorders, including, but not limited to, neurological tumors, cerebrovascular accidents and strokes, optic nerve disorders, compression syndromes of the optic nerve or optic chiasm, demyelinating diseases, and diseases of the retina.

The implementation may be in the form of a single-level neural network system or a hierarchical system. In the single-level system, all the input data, which are deemed relevant for the interpretation task, are inputted and processed simultaneously. In the hierarchical system, different input data types are modeled by dedicated separate subsystems, and these outputs are subsequently fused through a suitable computational architecture, to produce the final classification result.

The output module 28 creates a graphical representation of the visual field test data, such as isopter/scotoma plots, or gray scale or color-coded plots, with superimposed identification of the regions that the system classified as abnormal.

The automatic interpretation system is an expert system trained on a set of empirical, semi-empirical, and/or simulated data. The construction of a proper training database is essential for achieving good performance of the interpretation system (good sensitivity and specificity). The training database may contain all, or any, of the following types of visual field data:

(a) empirical data, i.e., data obtained for patients with normal and abnormal visual fields;

(b) semi-empirical data, i.e., data obtained by modification of the empirical data, as described above, by:

(1) emphasizing or de-emphasizing certain aspects of the visual field test to bring out the characteristic features of certain diseased states;

(2) adding noise or measurement uncertainty components which may be associated with a real visual field examination; and, (3) any other modification of the visual field test data and their associated classification; and, (c) simulated data, i.e., data that are constructed to simulate the real-world results of a visual field test for both normal and abnormal visual fields.

Training of the classification system is performed off-line with active participation of a human expert. That is, all visual field test data in the training database are examined by an expert and the medical diagnosis is verified and validated before the data is used to build the neural network model. The centralized processing enables collection of a large number of diverse examples of normal and abnormal visual field test data The novelty detection capability of the system alerts the system custodian to the necessity for expert examination of the novel data. After completion of such examination, the data may be included in the model by including the new data in the training database and re-training the system.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. A multiple site visual field testing system, comprising:

a plurality of electronic image display devices, each said display device being constructed and positioned to display an electronic image encompassing the visual field of at least one eye of a patient;

a plurality of response sensing devices, each said response sensing device being adapted to sense a patient's response to a visual stimulus and to generate a response signal;

a plurality of local signal processing systems, each said local processing system being connected to a respective said display device to generate said electronic image, each said local processing system being connected to a respective said response sensing device to receive said response signal;

a central processing system connectable to said plurality of local signal processing systems for controlling generation of said electronic images, and for receipt of said response signals from said plurality of local processing systems;

a neural network for automatic interpretation of said response signals; and a central data repository for collection of data from said response signals, and for repetitive training of said neural network.

2. A visual field testing system as recited in claim 1, wherein each said electronic image display device is a virtual reality device mounted in a substantially motionless relationship to the head of a patient, while allowing the head to move.

3. A visual field testing system as recited in claim 1, wherein said neural network is incorporated within said central processing system.

4. A visual field testing system as recited in claim 1, wherein said central data repository is incorporated within said central processing system.

5. A visual field testing apparatus as recited in claim 1, wherein said central processing system is programmable to vary at least one characteristic of each said electronic image.

6. A visual field testing apparatus as recited in claim 1, wherein said neural network is trained to analyze at least one characteristic of the visual field of each patient and render a diagnosis for each patient.

7. A visual field testing apparatus as recited in claim 6, wherein said visual field characteristic is the nature and extent of the peripheral field of vision of the patient.

8. A visual field testing apparatus as recited in claim 6, wherein said visual field characteristic is the nature and extent of the color vision of the patient.

9. A visual field testing apparatus as recited in claim 6, wherein said visual field characteristic is the nature and extent of the visual acuity of the patient.

10. A visual field testing apparatus as recited in claim 1, wherein said central processing system is connectable to said plurality of local signal processing systems via the Internet.

11. A method for automatically analyzing the visual fields of a plurality of patients, comprising:

providing an electronic image display device, a response sensing device, and a local signal processing device for each of a plurality of patients;

generating and displaying an electronic image for each patient;

sensing each patient's response to said electronic image and generating a response signal for each patient;

controlling said generation of each said electronic image and receiving each said response signal with a central processing system; and analyzing at least one characteristic of the visual field of each patient with a central neural network.

12. A method as recited in claim 11, further comprising varying at least one characteristic of said electronic image.

13. A method as recited in claim 11, further comprising connecting said central processing system to each said electronic image display device, response sensing device, and local signal processing device via the Internet, for controlling the generation of each said electronic image and receiving each said response signal.

* * * * *